(12) United States Patent
Habib et al.

(10) Patent No.: US 8,110,804 B2
(45) Date of Patent: Feb. 7, 2012

(54) THROUGH SUBSTRATE OPTICAL IMAGING DEVICE AND METHOD

(75) Inventors: Taufiq Habib, Gehrden (DE); Alex F. Schreiner, Hillsboro, OR (US); Jon Marson, Hillsboro, OR (US)

(73) Assignee: Viscom AG, Hannover (DE)

( * ) Notice: Subject to any disclaimer, the term of this patent is extended or adjusted under 35 U.S.C. 154(b) by 37 days.

(21) Appl. No.: 12/588,504

(22) Filed: Oct. 16, 2009

(65) Prior Publication Data

US 2010/0181483 A1 Jul. 22, 2010

Related U.S. Application Data

(63) Continuation of application No. PCT/EP2008/002969, filed on Apr. 15, 2008.

(60) Provisional application No. 60/912,092, filed on Apr. 16, 2007.

(51) Int. Cl.
*G01J 5/20* (2006.01)

(52) U.S. Cl. ............... 250/338.4; 356/237.1; 356/136; 250/332; 250/341

(58) Field of Classification Search ........... 356/237.1, 356/136; 250/332, 341
See application file for complete search history.

(56) References Cited

U.S. PATENT DOCUMENTS

| 3,645,631 | A | * | 2/1972 | Gupta | 356/136 |
| 5,272,342 | A | * | 12/1993 | Kotani | 250/341.4 |
| 5,981,949 | A | * | 11/1999 | Leahy et al. | 250/332 |
| 2005/0152146 | A1 | | 7/2005 | Owen et al. | |
| 2005/0219521 | A1 | | 10/2005 | Vollrath et al. | |
| 2005/0231713 | A1 | * | 10/2005 | Owen et al. | 356/237.1 |

FOREIGN PATENT DOCUMENTS

DE 19525770 8/1996
WO WO 2008/119550 A1 10/2008

OTHER PUBLICATIONS

International Search Report for PCT/EP2008/002969, dated Aug. 21, 2009, (3 pgs.).
Patent Cooperation Treaty, written opinion of the international searching authority for PCT/EP2008/002969, (7 pgs.).

* cited by examiner

*Primary Examiner* — David Porta
*Assistant Examiner* — Hugh H. Maupin
(74) *Attorney, Agent, or Firm* — Shlesinger, Arkwright & Garvey LLP

(57) ABSTRACT

A through-substrate optical imaging device for through-imaging of translucent work objects, includes a radiation source outputting radiation that will be transmissive through the work object and an imaging system configured for capturing inspection information from the radiation source through the work object. The radiation source is configured such that the radiation impinges on the surface of the work object under various angles of incidence. A method for through-substrate optical imaging of a translucent work object includes irradiating the translucent work object by radiation from a radiation source; capturing inspection information from the radiation source through the translucent work object, the inspection information being captured by an imaging system; and irradiating the translucent work object. The translucent work object is irradiated by radiation which impinges on the surface of the translucent work object under one of various angles of incidence and orientations.

25 Claims, 12 Drawing Sheets

Bad Bond
Frit Height exaggerated for display

Bad Bond

Frit Height exaggerated for display

Mostly collimated light is not affected by delamination.

Frit Height exaggerated for display

Widely scattered light is further scattered at delamination due to change in refractive index. This is manifested by changes in image intensity.

Frit Height exaggerated for display

THROUGH SUBSTRATE OPTICAL IMAGING DEVICE AND METHOD

CROSS-REFERENCE TO RELATED APPLICATIONS

This application is a continuation of application no. PCT/EP2008/002969, filed 15 Apr. 2008, which claims the convention priority of U.S. application No. 60/912,092, filed Apr. 16, 2007, and each of which is incorporated herein by reference.

FIELD OF THE INVENTION

The invention relates to a through-substrate optical imaging device for through-imaging of translucent work objects including a radiation source outputting radiation that will be transmissive through the work object, and to an imaging system configured for capturing inspection information from the radiation source through the work object for through-imaging of translucent work objects. Further, the invention relates to a through-substrate optical imaging method for through-substrate optical imaging of translucent work objects, wherein the work object is irradiated by radiation from a radiation source and wherein inspection information from the radiation source through the work object is captured by an imaging system.

BACKGROUND OF THE INVENTION

Through-substrate optical imaging devices include a radiation source outputting radiation that will be transmissive through the work object. Furthermore, the known devices include an imaging system configured for capturing inspection information from the radiation source through the work object.

There is a need for improved imaging systems, particularly inspection systems in the manufacturing of semiconductor devices to determine whether or not certain structures are present. Typically, the structures are defects. While the inventive subject matter may be used in various imaging or inspection applications, it will be illustrated herein in the context of a Micro Electro Mechanical System (MEMS) inspection.

The general structure of a Micro Electro Mechanical System (MEMS) device involves a device wafer, electronic or mechanical components located on the device wafer, a barrier surrounding the edge of the device wafer, and a cap wafer. During the assembly of the MEMS device, a frit is affixed to the bottom of the cap wafer. The cap wafer is then pressed down onto the device wafer causing the frit to create a bond with the device wafer.

In one method of determining if the device has seal integrity, a beam of infra-red (IR) or near infra-red (NIR) light is projected either through the top (toplight or Si Reflect Method) or the bottom (backlight, transmissive or Si-Thru method) of the wafer. On the top side of the wafer is a camera or photodetection device.

The standard method to detect seal defects is to project infrared or near infrared collimated light orthogonally to the device surface on one side to check for seal integrity. When the wafer is illuminated with infrared or near infrared collimated light, the seal extents and gross voids in the seal are easily detected.

Unfortunately, in this method illumination of the device wafer does not highlight subtle delamination between the seal and the device wafer to which the seal is bonded. This failure to highlight the subtle defects results because delaminations do not significantly affect transmission of the light passing through the device wafer and the frit. Accordingly, there is a need for improved inspection systems in MEMS inspections and other inspection applications.

OBJECTS AND SUMMARY OF THE INVENTION

It is an object of the invention to overcome the drawbacks of the prior art.

It is another object of the present invention to provide an improved through-substrate optical imaging device and method.

The inventive subject matter addresses the foregoing need by providing improved imaging devices for use in through imaging of translucent objects. Usually these translucent through-objects are semiconductor devices and similar work objects. In certain respects, the inventive subject matter is directed to a device and method for creating a substantially non-collimated light source that will allow a determination of whether or not certain structures are present in an object under inspection. In one possible application, the device and method are directed to detection of subtle delaminations between a device wafer and the frit.

The invention is based on the idea to irradiate the work object with a beam such that the angle of incidence of the light ray varies from the normal. If e.g. a light source is used as a radiation source, a plurality of light rays is directed onto the surface of the work object such that at least some of the light rays impinge on the surface in a non-perpendicular manner. It has been found that in this way the optical imaging is improved substantially, in particular with respect to image quality and detection of fine structures, in particular subtle delaminations. Consequently, the inventive device allows for optical imaging with a high image quality and therefore for the detection of features, either intended features or defects, in particular of delamination in a wafer structure.

According to a preferred further embodiment of the invention beam forming means or device are provided for forming the beam of a radiation source such that the radiation impinges on the surface of the work object under various angles of incidence. According to the respective application, the beam forming means or device may be chosen within wide ranges.

In order to provide a relatively simple and cost-effective beam forming means, according to a further preferred embodiment the beam forming means includes at least one optical diffuser which is located between the radiation source and the work object, such that the diffused radiation impinges on the surface of the work object. The diffuser has the effect that a collimated or near-collimated beam, for example a light beam, is diffused so that the angle of incidence of the light rays varies from the normal and the light rays or at least some of the light rays impinge onto the surface of the work object under various angles.

According to an alternate embodiment, the radiation source or a radiation source point of the radiation source is angularly positionable relative to the work object, such that in different angular positions of the radiation source or the radiation source point of the radiation source the radiation impinges on the surface of the work object under different angles of incidence. In this embodiment a collimated or near-collimated light source may be used without a diffuser. Various angles of incidence are obtained in this embodiment by angularly positioning the radiation source or the radiation source point relative to the work object. In this way, the same effect is obtained as in the embodiment using the diffuser.

Within the terms of the invention the radiation source point is defined as a point of the radiation source from which the radiation leaves the radiation source or a radiation guide means or device, for example an optical fiber means or optical fiber device. Consequently, the radiation source and the radiation source point may be spaced apart from each other.

According to a further development, in particular of the beforementioned embodiment, the radiation source or the radiation source point of the radiation source is positionable in a plane (X-Y plane) substantially parallel to the surface of the work object, such that various locations of the work object may be irradiated in various positions and/or orientations of the radiation source or the radiation source point relative to the work object. In this embodiment, during an inspection of the work object the radiation source or the radiation source point scans the surface of the work object continuously or in a step-wise manner in order to have the work object inspected at various locations.

Basically, any suitable radiation source may be used. According to a further preferred embodiment the radiation source is a light source. In particular, for inspection of semiconductor devices, light in the infrared or near-infrared (NIR) range may be used.

According to a further preferred embodiment the light-source is a semiconductor-based light-source. Suitable semiconductor-based light-sources are widely available and relatively cost effective.

According to a further preferred embodiment at least two radiation sources or radiation source points are provided which are configured for preferably simultaneously irradiating the work object from at least two locations. In this embodiment detection of subtle structures is further improved. If e.g. a work object is inspected using two or more light sources, it may occur that an edge of an internal structure of the work object is parallel to the light rays from one light source and therefore is difficult to detect. By using at least the second light source irradiating the work object under a different angle, detection of corresponding edges or similar structures is simplified.

An inventive through-substrate optical imaging method for through-imaging of a translucent work has likewise been achieved.

According to an embodiment of the inventive method for through-substrate optical imaging of translucent work objects, the work object is irradiated by radiation from a radiation source, and inspection information from the radiation source through the work object is captured by an imaging system. In that manner the work object is irradiated by radiation which impinges on the surface of the work objects under various angles of incidence and/or orientations.

According to another embodiment of the inventive method the beam of the radiation source is formed by beam forming means, such that the radiation impinges on the surface of the work object under various angles of incidence.

According to a further embodiment of the inventive method a diffuser is used which is located between the radiation source and the work object, such that the diffused radiation impinges on the surface of the work object.

According to another embodiment of the inventive method the radiation source or a radiation source point of the radiation source is angularly positioned relative to the work object, such that in different angular positions of the radiation source or the radiation source point the radiation impinges on the surface of the work object under different angles of incidence.

According to a yet further embodiment of the inventive method the radiation source or a radiation source point of the radiation source is positioned in a plane (X-Y plane) substantially parallel to the surface of the work object, such that various locations of the work object may be irradiated in various positions and/or orientations of the radiation source or the radiation source point relative to the work object.

According to another embodiment of the inventive method a light source is used as a radiation source.

According to a still further embodiment of the inventive method a semiconductor-based light-source is used as a light source.

According to another embodiment of the inventive method at least two radiation sources or radiation source points are used which are configured for preferably simultaneously irradiating the work object from at least two locations.

In certain embodiments, the inventive subject matter is directed to using collimated light, an optical system for diffusing the light, and an image processing system for detecting subtle delaminations between the device wafer and the frit.

Alternate embodiments include the use of a collimated light source, but, adjusting the light with beam forming methods so that the angle of incidence of the light rays varies from the normal. This adjustment eliminates the need for an optical system diffuser.

The foregoing is not intended to be an exhaustive list of embodiments and features of the present inventive concept. Persons of ordinary skill in the art are capable of appreciating other embodiments and features from the following detailed description in conjunction with the drawings.

The invention will now be explained in greater detail with reference to the accompanying drawings wherein all features described, illustrated in the drawings or claimed in the claims constitute the subject matter of the invention, either taken alone or in arbitrary combination with each other, regardless of their combination in the claims and the references of the claims as well as regardless of their description in the specification and their illustration in the drawings.

DETAILED DESCRIPTION OF THE INVENTION

As indicated above, the present invention is illustrated in the context of an inspection of a Micro Electro Mechanical Device (MEMS), but is not intended to be limited to this inspection application.

Figure 1A:
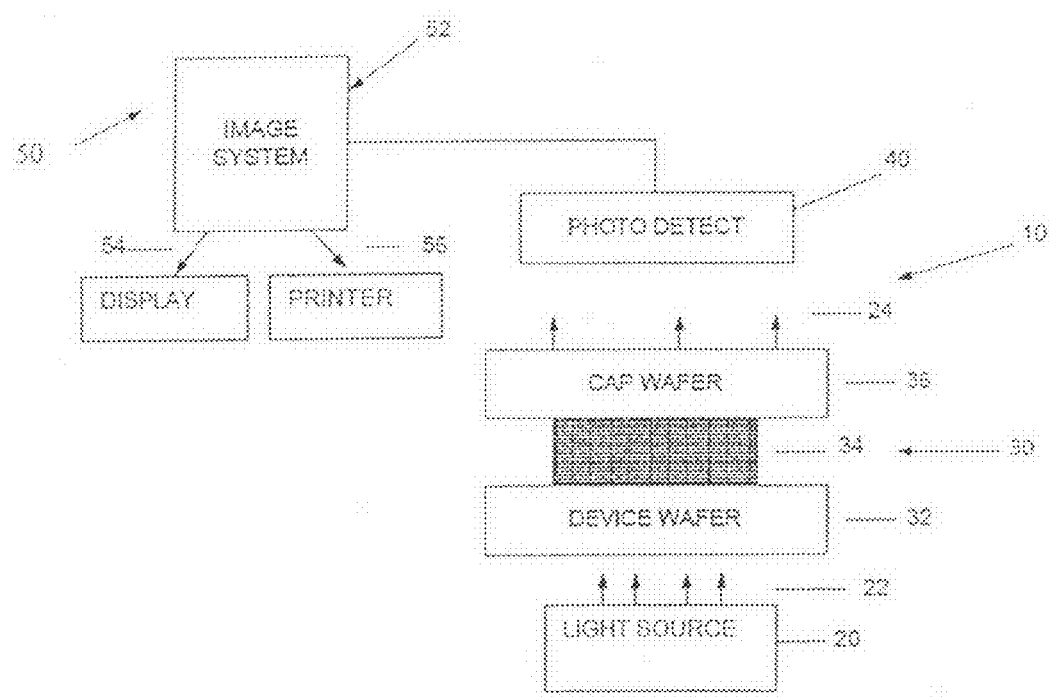
FIG. 1A shows a PRIOR ART assembly that is used to detect gross voids using collimated light.

FIG. 1A depicts a PRIOR ART collimated light source 20, a work object 30 interposed between the light source 20, a photodetector 40, and an imaging system 50. Exemplary wavelengths of the light source 20 are in the infrared or near infrared range. The work object 30 consists of a device wafer 32, a frit 34, and a cap wafer 36. The work object 30, can be any device with one or more layers that are translucent to the light emitted from the light source 20. The photodetector 40 is connected to the imaging system 50, which may consist of an image processing system 52, and a display 54, or a printer 56. Gross voids or seal extents are only detected when the collimated or near-collimated light 32 passes through the device wafer 32, the frit 34, and the cap wafer 36. The modified non-collimated light 24 creates an image on the photodetector 40. The output from the photodetector 40 is processed by the imaging system.

Figure 1B:
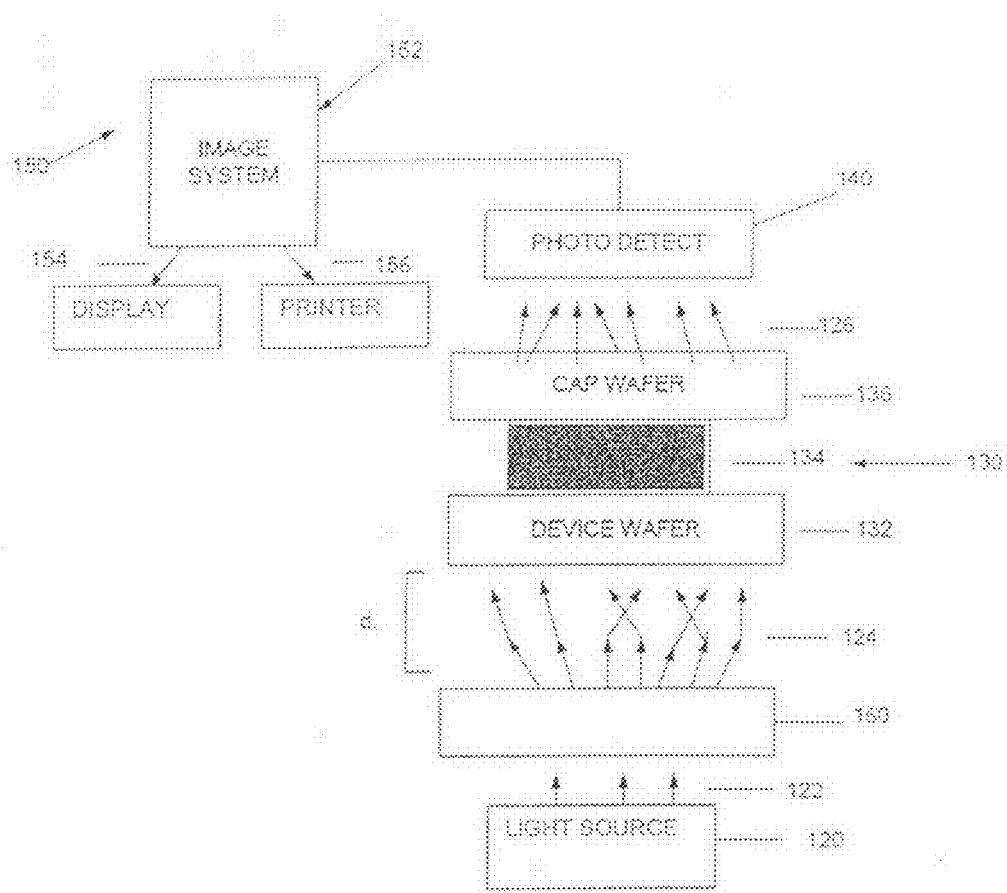
FIG. 1B is one possible embodiment of an inventive device that is used to detect subtle delaminations in a work object using non-collimated light created by an optical assembly.

FIG. 1B depicts one possible embodiment of an inventive system that includes a collimated light source 120, an optical system 160, a work object 130, a photodetector 140, and an imaging system 150. The wavelengths of the collimated light source 120 are in the infrared or near infrared range. The collimated light source 120 projects collimated rays 122 through an optical assembly 160. The optical assembly 160 receives a light beam from the collimated light source that is slightly smaller than the area being detected by the imaging system 150. The optical assembly 160 modifies the collimated beam to create a formed beam 124. This diffused beam 124 rays strike the device wafer at angles that are other than normal. The beam 124 then travels through the device wafer 132, the frit 134, and the cap wafer 136. The exiting diffused beams 126 are detected by the photodetector 140 suitable photodetector including, for example, a CMOS or CCD image sensor. The output from the photodetector 140 is connected to the imaging system 150. The imaging system 150 includes an image processor 152. The system may further include a display 154 and/or a printer 156. The photodetector 140 and imaging system 150 may not be limited to a CMOS sensor, but may also employ other photodetection means or device, such as photomultiplier tubes, or cryogenic particle detectors.

Figure 2A:
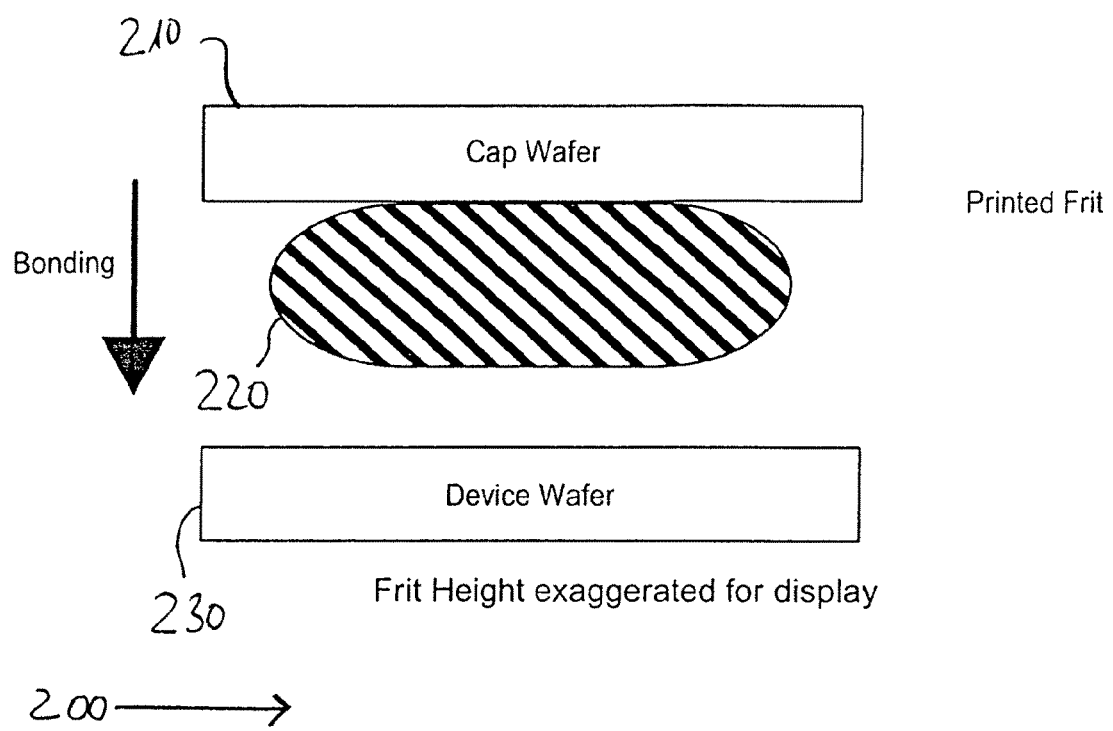
FIG. 2A shows a detailed view of the work object prior to assembly.
Figure 2B:
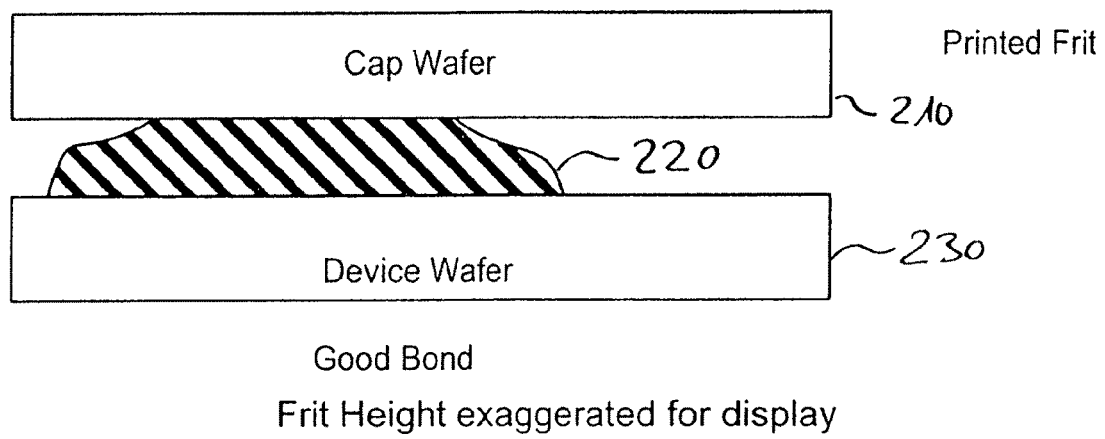
FIG. 2B shows a detailed view of the work object after assembly where there is a proper bond between the frit and the device wafer.
Figure 2C:
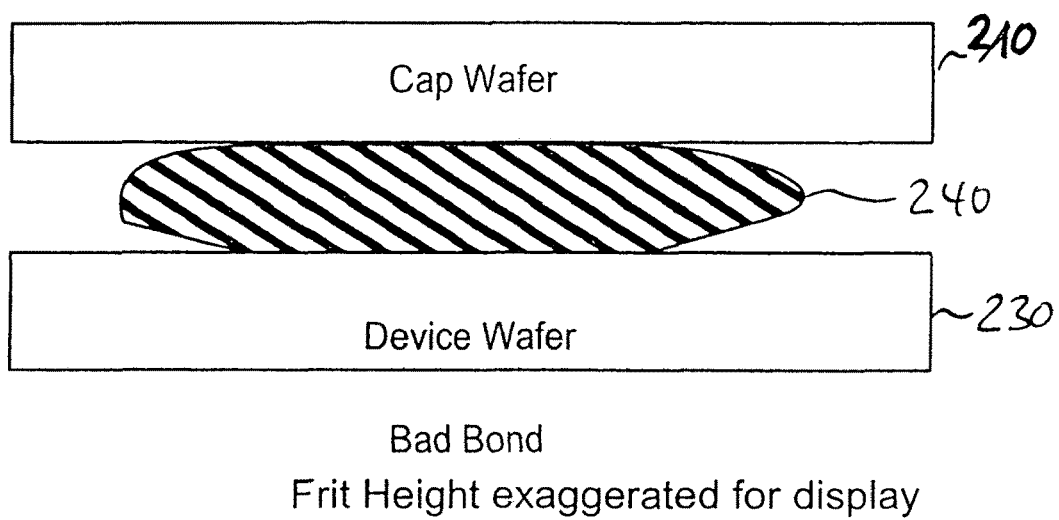
FIG. 2C shows a detailed view of the work object after assembly where there is an improper bond between the frit and the device wafer caused by subtle delamination on the edges.
Figure 2D:
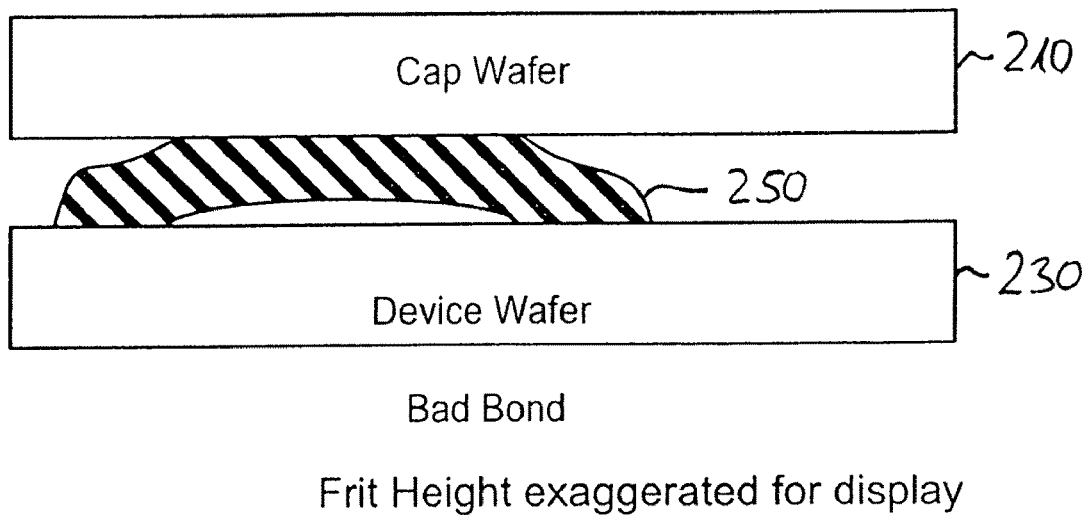
FIG. 2D shows another detailed view of the work object after assembly where there is an improper bond between the frit and the device wafer caused by subtle delamination internally.

FIGS. 2A, 2B, 2C, and 2D, show a side view of the system. FIG. 2A shows a side view of the work object prior to the bonding, the work object consisting of the cap wafer 210, the printed frit 220, and the device 230. In FIG. 2B, an exemplary view of a good bond is shown. The printed frit 220 is compressed on the device wafer 230 without any voids or delaminations. In FIG. 2C a poor quality bond (e.g., bad bond) is shown with delaminations 240 in the area between the printed frit and the device wafer. In FIG. 2D a poor quality bond is shown with a void 250 between the device wafer and the printed frit.

Figure 3A:
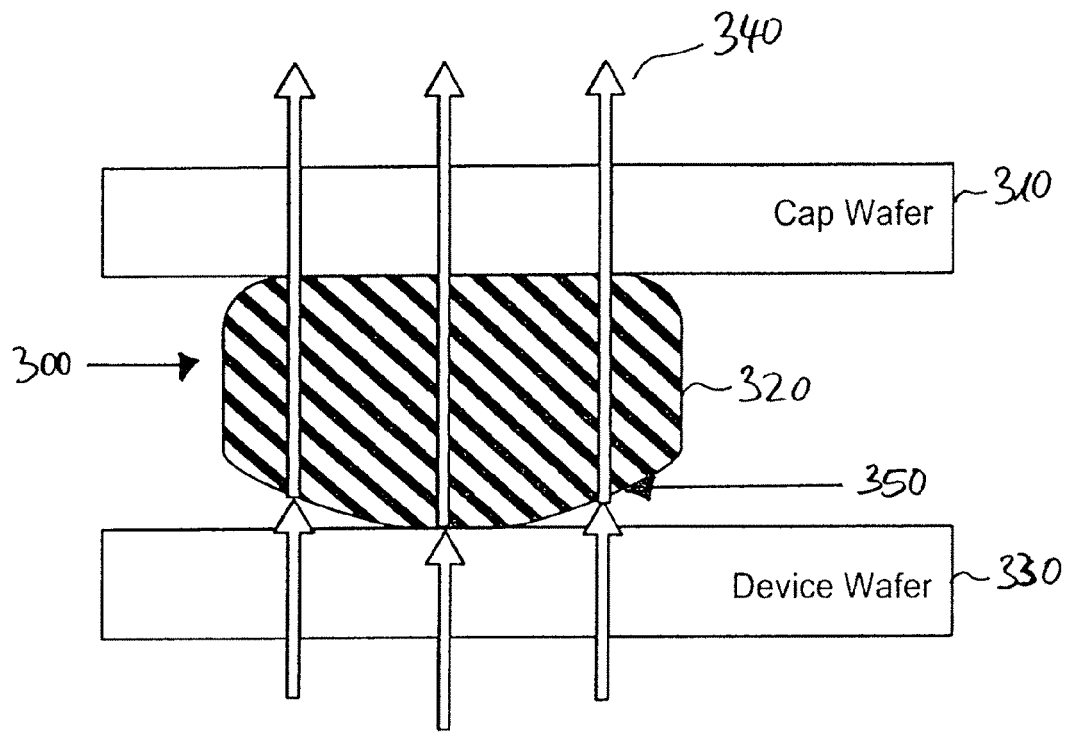
FIG. 3A shows a detailed view of the ray pattern of collimated light passing through the device wafer, the frit, and the cap wafer.
Figure 3B:
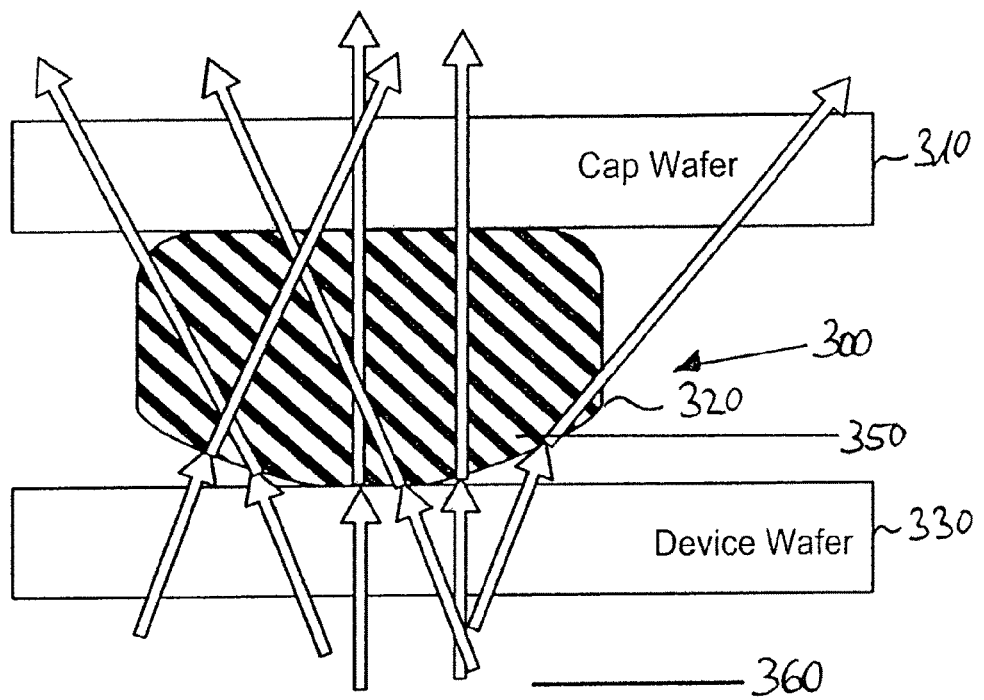
FIG. 3B shows a detailed view of the ray pattern of the non-collimated light passing through the device wafer, the frit, and the cap wafer.

FIGS. 3A and 3B depict ray tracing through the device wafer, the printed frit, and the cap wafer. In FIG. 3A, a view of collimated rays 340 is shown projected through the device wafer 330, the printed frit 320, and the cap wafer 310. A collimated ray strikes an area of subtle delamination 350 at a normal angle, but is not deflected. The ray then continues through the printed frit 320, exiting the cap wafer in a normal fashion 310. This is the ray path of the PRIOR ART assembly, as shown in FIG. 1A.

In FIG. 3B, non-collimated rays 360 strike the device wafer 330. The rays then strike the area of subtle delamination 350 and are deflected according to Snells law (e.g. $n_1 \sin \theta_1 = n_2 \sin \theta_2$). The non-collimated rays 360 can trace two different paths. The first path is through the device wafer 330, the printed frit 320, and the cap wafer 310. The second path is through the device wafer 330, the area of subtle delamination 350, the printed frit 320, and the cap wafer 310. The exit angle of the first path and the second path differ by refractive index of the area of subtle delamination 350. It is this difference in the exit angle that is captured by the photodetector and displayed by the image processing system. It is also possible for the exit angle to be affected by texture differences due to delamination as a result of bad seal bonding.

Figure 4:
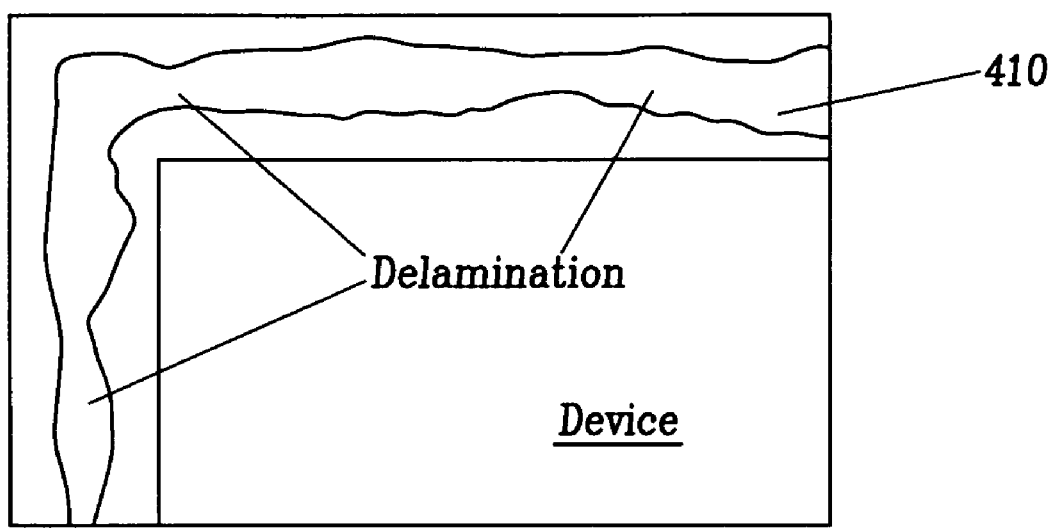
FIG. 4 shows an exemplary image of the delamination image patterns created by the passing of non-collimated light through the device wafer, the frit, and the cap wafer, and these delamination image patterns displayed after detection from an image processing system.

In FIG. 4, the photodetector and image processing system displays the areas of non-collimated light 410 that are indicative of subtle delamination. The size and intensity of these areas are dependent on the size and structure of the areas of subtle delamination. The method of determining if there is a defect is typically done by comparing a known or reference image with the actual image. With the use of CCD capture technology and image processing systems, comparing a reference image to the actual image may be done using software.

Now referring back to FIG. 1B, exemplary solid-state light sources, systems and applications in which the inventive subject matter contemplated herein may be used include those set forth in U.S. National Phase patent application Ser. No. 10/984,589, filed May 8, 2003, entitled "High Efficiency Solid-State Light Source and Methods of Use and Manufacture," published as US2005/0152146A1 on Jul. 14, 2005, which is incorporated herein by reference in its entirety for all its teachings. U.S. National Phase patent application Ser. No. 10/984,589 discloses, among other things, high-intensity light sources that are formed by a micro array of semiconductor-based light sources, such as LEDs, laser diodes, or VCSEL placed densely on a substrate to achieve power density output of at least 50 mW/cm$^2$ (i.e., 50 mW/cm squared).

Exemplary solid-state light sources, systems and applications in which the inventive subject matter contemplated herein may be used include those disclosed by U.S. Nonprovisional patent application Ser. No. 11/109,903, filed Apr. 19, 2005, entitled "Imaging Semiconductor Structures Using Solid State Illumination," published as US2005/0231713A1 on Oct. 20, 2005, which is incorporated herein by reference. U.S. Non-provisional patent application Ser. No. 109,903 discloses, among other things a solid state light source that irradiates selected semiconductor-based structures via a fiber optic light guide and a lens system. The source's radiation is directed to structures via an internal beam splitter in the lens system. The radiation, so directed, generally is reflected by structures at various intensities (e.g., depending on the bond characteristics and other features and defects of the semiconductor structures), so as to travel back up through the lens system, to a camera, such camera being based on or using one or more solid state imaging devices, e.g., CCD or CMOS detectors. The camera preferably detects such reflected radiation of one or more wavelengths. Via such detection, an image of the structures is captured. The image, so captured, may be provided for further processing via, e.g., computer The captured image, so processed or otherwise, may be employed for test and quality control, toward identifying relevant features of such structures e.g., where such relevant features are associated with bonded or stacked layers (e.g., in the interfacing layer(s) of bonded or stacked substrates or in the bond itself) or with other bonded or stacked materials.

U.S. Provisional Patent Application No. 60/888,874, filed Feb. 8, 2007 entitled "Semiconductor Light Sources, Systems, and Methods" is incorporated herein by reference.

Optical diffusers necessary to create the non-collimated beam from the collimated beam examples of which being: a holographic diffuser or an optical glass diffuser.

An alternate embodiment of the inventive subject matter involves the adjustment of the collimated or near-collimated light source. For example, the collimated or near-collimated light source is rotated off axis such as to have the beam strike the device wafer at an angle other than normal to the wafer surface. The beam refracts through the wafer in the same fashion as a diffuse ray passing through the surface off the normal axis. This eliminates the need for an optical system to diffuse the light. Implementations of this embodiment may include a mechanical adjustment of the light source or the adjustment of the mount holding the wafer.

Figure 5A:
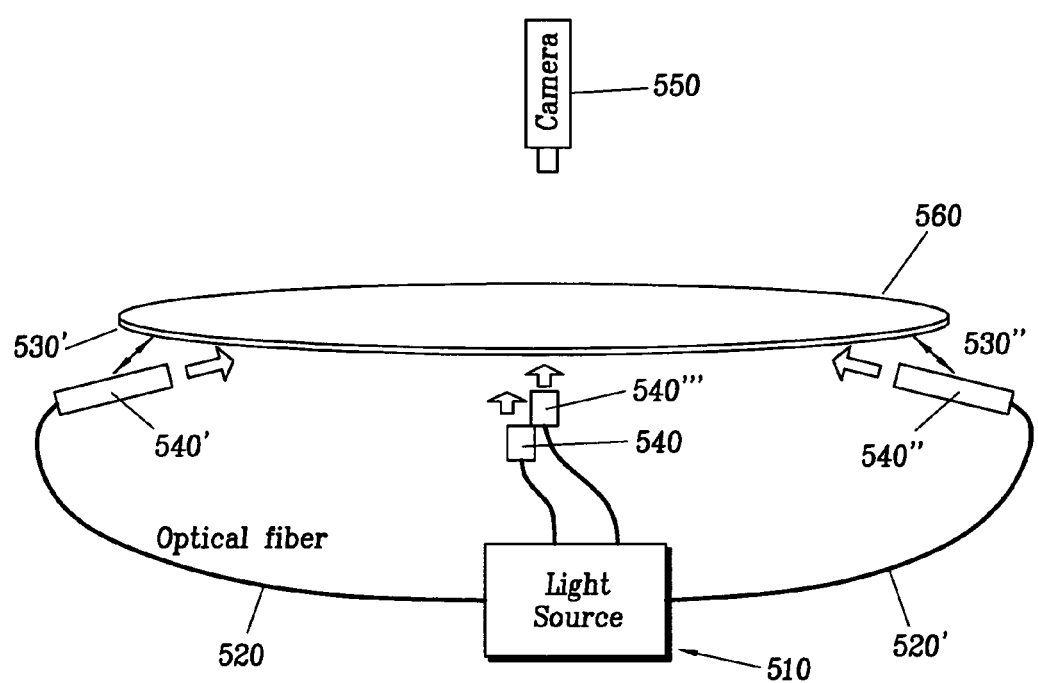
FIG. 5A shows a diagram of a low angle halogen light source illuminating a wafer without a metal layer in the wafer.

Referring to FIG. 5A, an exemplary implementation of the alternate embodiment for use with silicon wafers that do not have metal layers is shown. This implementation consists of a collimated light source 510, fiber bundle 520, and the light source point 540, with the light source point 540 positioned at an angle 530 to the underside of the wafer 560. An imaging system 550 captures and processes the image in a manner previously described. An implementation of the light source 510 consists, for example, of a halogen light (model MHF-D-100-CR manufactured by Moritex, www.moritex.co.jp) with a silicon filter to pass near infrared light. The light source 510 is typically 5 mm in diameter, but may be of a greater or lesser diameter. The coherent light from the light source point 540 illuminates the wafer at an angle 530 from 5 to 25 degrees relative to the surface of the wafer 560. The light source point 540 is located approximately 100 mm from the center of the wafer 560. The light source point 540 is positioned at various points 540', 540", and 540'" and at various angles 530', 530", 530'" to observe the areas of delamination with the camera 550. Alternately a fiber ring (not shown) with uniform illumination that is located approximately 20-50 mm. from the surface of the wafer 560 may be utilized.

Figure 5B:
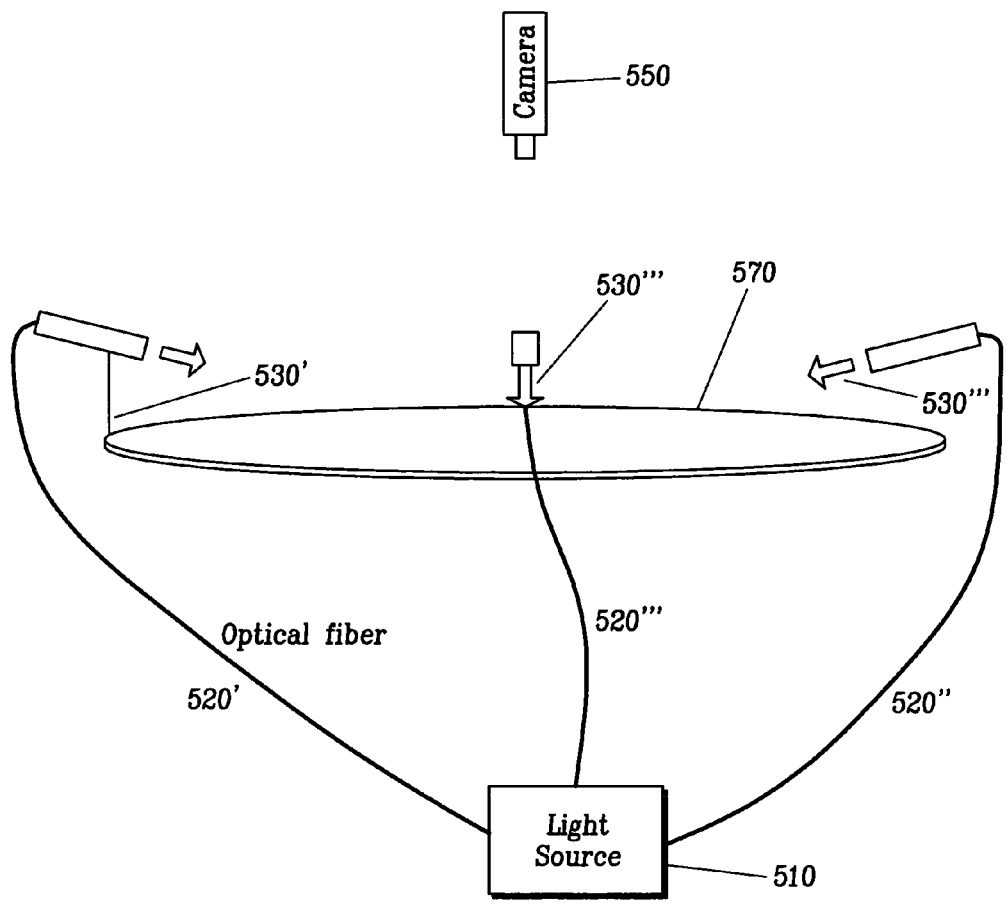
FIG. 5B shows a diagram of a low angle light source illuminating a wafer with a metal layer in the wafer.

Referring to FIG. 5B, the implementation of the alternate embodiment for use with silicon wafers that have metal layers is shown. This implementation consists of a collimated light source 510, fiber bundle 520, and the light source point 540, with the light source point 540 positioned at an angle 530 to the top side of the wafer 570. An imaging system 550 captures and processes the image in a manner previously described. An implementation of the light source 510 a halogen light (model MHF-D-100-CR manufactured by Moritex, www.moritex.co.jp) with a silicon filter to pass near infrared light. The light source 510 is typically 5 mm in diameter, but may be of a greater or lesser diameter. The coherent light from the light source point 540 illuminates the wafer at an angle 530 from 5 to 25 degrees relative to the surface of the wafer 560. The light source point 540 is located approximately 100 mm from the center of the wafer 560. Alternately a fiber ring (not shown) with uniform illumination that is located approximately 20-50 mm from the surface of the wafer 560 may be utilized.

Figure 6:
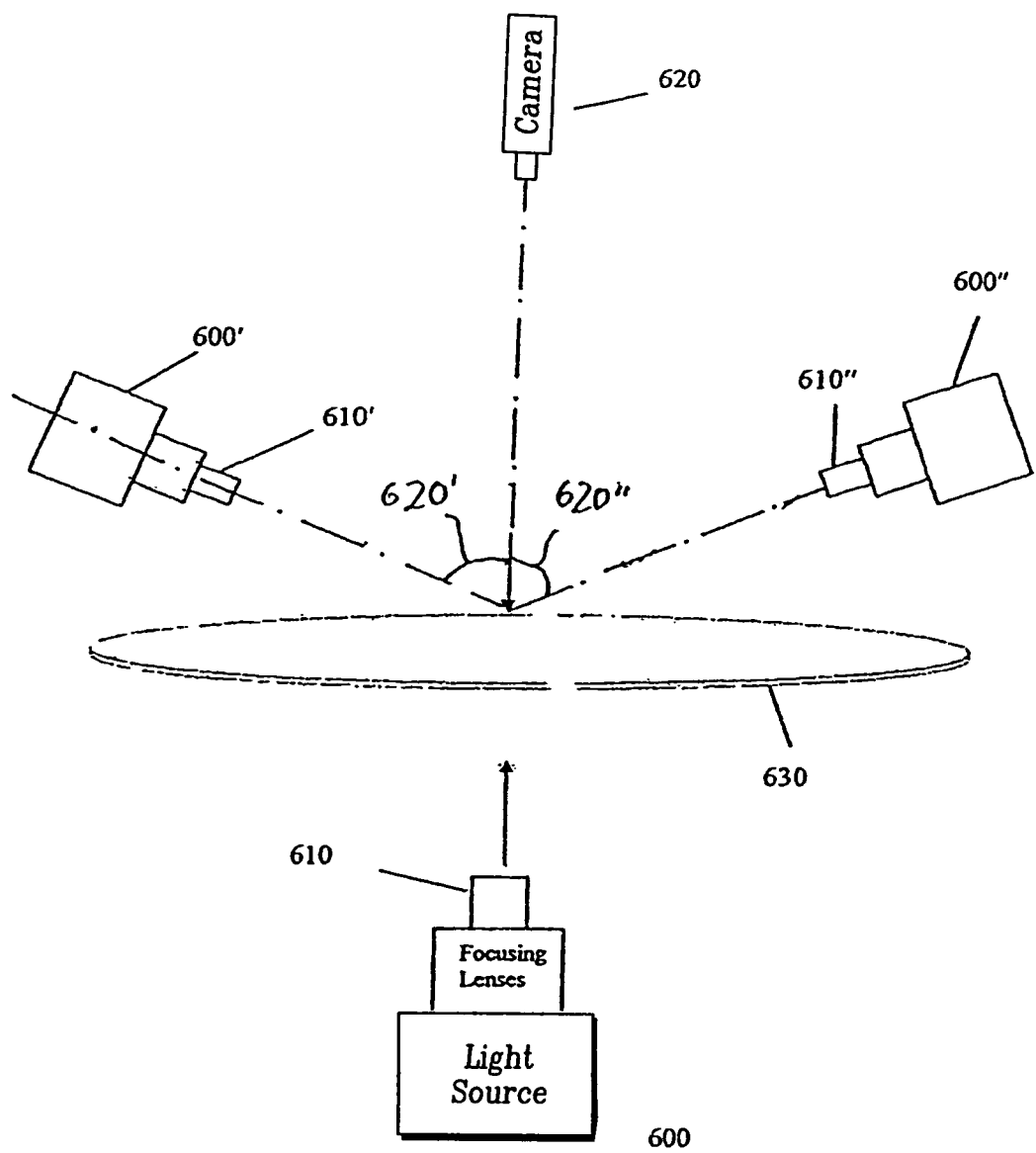
FIG. 6 shows a diagram of a low angle semiconductor light matrix illuminating a wafer with a metal layer in the wafer.

Now referring to FIG. 6 a semiconductor light matrix 600 (manufactured by Phoseon Technology Inc., Beaverton, Oreg., www.phoseon.com) is shown illuminating the wafer 630. The output of the semiconductor light matrix 600 is coupled to focusing lens 610. The semiconductor light matrix 600 and focusing lens 610 combination is positioned at an angle 620 from the wafer 630 surface. The camera 640 takes images of wafer 630 surface to detect areas of subtle delamination. The semiconductor light matrix 600 is positioned at various points 600', 600" and at various angles 620', 620" such that the entire wafer may be inspected. The use of a semiconductor light matrix 600 can also be configured to illuminate the top of the wafer 630 for metal layer wafers or illuminate the bottom of the wafer 630 in the same manner as depicted in FIGS. 5A and 5B.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. A through-substrate optical imaging device for through-imaging detection of bonding delamination of a translucent work object including two substrates bonded together with a seal element, comprising:
   a) a radiation source provided for outputting radiation which will be transmissive through the work object;
   b) an imaging system configured for capturing inspection information from the radiation source through the work object, the captured inspection information including differences in exit angles of the radiation by refractive index of bonding areas;
   c) the radiation source being configured such that the radiation impinges on a surface of the work object under various angles of incidence and orientations; and
   d) an image processing software for processing the captured inspection information to determine if there is a bonding defect between the two substrates.

2. Device as claimed in claim 1, wherein:
   a) the radiation source is one of a collimated and a substantially collimated radiation source.

3. Device as claimed in claim 1, wherein:
   a) a beam forming device is provided for forming the beam of the radiation source such that the radiation impinges on the surface of the work object under various angles of incidence.

4. Device as claimed in claim 3, wherein:
   a) the beam forming device includes at least one optical diffuser which is located between the radiation source and the work object, such that the diffused radiation impinges on the surface of the work object.

5. Device as claimed in claim 1, wherein:
   a) one of the radiation source and a radiation source point of the radiation source is angularly positionable relative to the work object, such that in different angular positions of the one of the radiation source and the radiation source point the radiation impinges on the surface of the work object under different angles of incidence.

6. Device as claimed in claim 5, wherein:
   a) the one of the radiation source and the radiation source point is positionable in a plane (X-Y plane) substantially parallel to the surface of the work object, such that various locations of the work object may be irradiated in various positions and orientations of the one of the radiation source and the radiation source point relative to the work object.

7. Device as claimed in claim 1, wherein:
a) the radiation source is a light source.

8. Device as claimed in claim 7, wherein:
a) the light source is a semiconductor-based light-source.

9. Device as claimed in claim 1, wherein:
a) the radiation source includes at least one of two radiation sources and a radiation source point that are configured for simultaneously irradiating the work object from at least two locations.

10. Device as in claim 1, wherein:
a) the image processing software utilizes the size and intensity of the captured inspection information to determine if there is a subtle delamination.

11. Method as claimed in claim 10, wherein one of:
a) a beam of the radiation source is formed by a beam forming device, such that the radiation impinges on the surface of the translucent work object under various angles of incidence;
b) a diffuser is used which is located between the radiation source and the translucent work object, such that the diffused radiation impinges on the surface of the translucent work object;
c) one of the radiation source and a radiation source point of the radiation source is angularly positioned relative to the translucent work object, such that in different angular positions of the one of the radiation source and the radiation source point the radiation impinges on the surface of the translucent work object under different angles of incidence; and
d) the one of the radiation source and the radiation source point of the radiation source is positioned in a plane (X-Y plane) substantially parallel to the surface of the translucent work object, such that various locations of the translucent work object may be irradiated in one of various positions and orientations of the one of the radiation source and the radiation source point relative to the translucent work object.

12. Device as in claim 1, wherein:
a) the image processing software compares the captured inspection information with a reference image to determine if there is a bonding defect.

13. A method for through-substrate optical imaging detection of bonding delamination of a translucent work object including two substrates bonded together with a seal element, comprising:
a) irradiating the translucent work object by radiation from a radiation source, the translucent work object being irradiated by radiation which impinges on a surface of the translucent work object under one of various angles of incidence and orientations;
b) capturing inspection information including differences in exit angles by refractive index of bonding areas from the radiation source through the translucent work object, the inspection information being captured by an imaging system; and
c) processing the captured inspection information to determine if there is a bonding defect.

14. Method as claimed in claim 13, wherein:
a) a beam of the radiation source is formed by a beam forming device, such that the radiation impinges on the surface of the translucent work object under various angles of incidence.

15. Method as claimed in claim 14, wherein:
a) a diffuser is used which is located between the radiation source and the translucent work object, such that the diffused radiation impinges on the surface of the translucent work object.

16. Method as claimed in claim 13, wherein:
a) one of the radiation source and a radiation source point of the radiation source is angularly positioned relative to the translucent work object, such that in different angular positions of the one of the radiation source and the radiation source point the radiation impinges on the surface of the translucent work object under different angles of incidence.

17. Method as claimed in claim 13, wherein:
a) the one of the radiation source and the radiation source point of the radiation source is positioned in a plane (X-Y plane) substantially parallel to the surface of the translucent work object, such that various locations of the translucent work object may be irradiated in one of various positions and orientations of the one of the radiation source and the radiation source point relative to the translucent work object.

18. Method as claimed in claim 13, wherein:
a) a light source is used as a radiation source.

19. Method as claimed in claim 18, wherein:
a) a semiconductor-based light-source is used as the light source.

20. Method as claimed in claim 13, wherein:
a) one of two radiation sources and a radiation source point are used which are configured for irradiating the translucent work object from at least two locations.

21. Method as claimed in claim 20, wherein:
a) the one of two radiation sources and a radiation source point are configured for simultaneously irradiating the translucent work object from at least two locations.

22. Method as in claim 13, wherein:
a) the size and intensity of the captured inspection information are indicative of subtle delamination.

23. Method as in claim 13, wherein:
a) processing the captured inspection information includes utilizing the size and intensity of the captured inspection information to determine if there is a subtle delamination.

24. Method as in claim 13, wherein:
a) processing the captured inspection information includes comparing the captured inspection information with a reference image to determine if there is a bonding defect.

25. A method for through-substrate optical imaging detection of bonding delamination of a translucent work object including two substrates bonded together by a seal element, comprising:
a) irradiating the translucent work object by radiation from a radiation source, the translucent work object being irradiated by radiation which impinges on a surface of the translucent work object under one of various angles of incidence and orientations;
b) capturing inspection information including differences in exit angles of the radiation by refractive index of bonding areas through the translucent work object, the inspection information being captured by an imaging system; and
c) displaying the captured inspection information which provides information related to a bonding delamination of the seal element.

* * * * *